(12) United States Patent
Dow et al.

(10) Patent No.: US 12,140,522 B2
(45) Date of Patent: Nov. 12, 2024

(54) METHOD AND APPARATUS FOR MONITORING MICROBIAL CONTAMINANTS IN AN INDUSTRIAL PROCESS

(71) Applicant: CELLFACTS ANALYTICS LIMITED, Coventry (GB)

(72) Inventors: Crawford Dow, Coventry (GB); Alexander Boehler, Bad Kreuznach (DE)

(73) Assignee: Alexander Boehler (DE)

( * ) Notice: Subject to any disclaimer, the term of this patent is extended or adjusted under 35 U.S.C. 154(b) by 881 days.

(21) Appl. No.: 17/286,294

(22) PCT Filed: Oct. 18, 2018

(86) PCT No.: PCT/EP2018/078660
§ 371 (c)(1),
(2) Date: Apr. 16, 2021

(87) PCT Pub. No.: WO2020/078560
PCT Pub. Date: Apr. 23, 2020

(65) Prior Publication Data
US 2021/0389224 A1    Dec. 16, 2021

(51) Int. Cl.
*G01N 15/14* (2024.01)
*C12Q 1/22* (2006.01)
(Continued)

(52) U.S. Cl.
CPC .............. *G01N 15/14* (2013.01); *C12Q 1/22* (2013.01); *C12Q 3/00* (2013.01);
(Continued)

(58) Field of Classification Search
None
See application file for complete search history.

(56) References Cited

U.S. PATENT DOCUMENTS

| 3,939,409 A | 2/1976 | Hogg |
| 6,614,215 B1 | 9/2003 | Wood |

(Continued)

FOREIGN PATENT DOCUMENTS

| CN | 107340226 A | 11/2017 |
| DE | 102004063110 | 7/2006 |

(Continued)

OTHER PUBLICATIONS

Agarwal et al.; Inhaled bacteriophage-loaded polymeric Microparticles ameliorate acute lung infections; Nature Biomedical Engineering; Vo. Nov. 2, 2018; 12 pages.

(Continued)

*Primary Examiner* — Cassandra F Cox
(74) *Attorney, Agent, or Firm* — Womble Bond Dickinson (57) ABSTRACT

An exemplary embodiment of an apparatus for detecting microbiological activity in an industrial process may include a plurality of satellite units, a processing unit, and a main analysis unit. Each satellite unit may be configured to sample a liquid from the industrial process at a plurality of respective locations, periodically analyse a sample, carry out an impedance analysis to count and measure the size of particles passing through an orifice, and generate sample results data corresponding to the number and size of particles in each sample. The processing unit may be configured to compare the sample results data to a predetermined criterion and to generate an alert signal if the particle data is outside of the predetermined criterion. The main analysis unit may be configured to carry out a combined impedance and electromagnetic emission analysis of a sample of liquid from the industrial process following generation of the alert signal.

20 Claims, 5 Drawing Sheets

(51) Int. Cl.
*C12Q 3/00* (2006.01)
*G01N 35/00* (2006.01)
*G01N 15/10* (2006.01)

(52) U.S. Cl.
CPC .............. *G01N 35/00722* (2013.01); *G01N 2015/1024* (2024.01); *G01N 2015/1029* (2024.01); *G01N 2015/1486* (2013.01); *G01N 2015/1493* (2013.01); *G01N 2035/009* (2013.01)

(56) References Cited

U.S. PATENT DOCUMENTS

2010/0271053 A1    10/2010   Xu et al.
2018/0333724 A1*   11/2018   Hull .................. G01N 15/0266

FOREIGN PATENT DOCUMENTS

| EP | 0844475 | A2 | 5/1998 |
|----|---------|-----|--------|
| EP | 1398043 | A2 | 3/2004 |
| GB | 2337583 | A | 11/1999 |
| GB | 2567635 | A | 4/2019 |
| JP | H08285759 | A | 11/1996 |
| WO | 2007087676 | A1 | 8/2007 |
| WO | 2009132362 | A3 | 1/2010 |
| WO | 2018184073 | A1 | 10/2018 |

OTHER PUBLICATIONS

Patent Cooperation Treaty; International Search Report; dated Sep. 24, 2019; 5 pages.
Patent Cooperation Treaty; Written Opinion of the International Searching Authority; dated Sep. 24, 2019; 12 pages.
United Kingdom Intellectual Property Office; Search Report under Section 17(5); dated Mar. 20, 2018; 5 pages.
United Kingdom Intellectual Property Office; Search Report under Section 17(6); dated Dec. 11, 2018; 2 pages.
United Kingdom Intellectual Property Office; Search Report under Section 17(6); dated Dec. 14, 2018; 2 pages.

* cited by examiner

| Satellite | Sample | Mode | Area |
|---|---|---|---|
| 202a | P1 | A | X |
| 202a | P2 | B | Y |
| 202a | P3 | C | Z |
| | | | |

METHOD AND APPARATUS FOR MONITORING MICROBIAL CONTAMINANTS IN AN INDUSTRIAL PROCESS

CROSS REFERENCE TO RELATED APPLICATIONS

This application is a National Stage of PCT Application No. PCT/EP2018/078660 filed on Oct. 18, 2018 which is incorporated herein by reference in its entirety.

FIELD OF THE DISCLOSURE

At least an embodiment of the present disclosure may be concerned with a method and apparatus for monitoring microbial contaminants in an industrial process. More specifically, at least an embodiment of the present disclosure may be concerned with an apparatus and process which utilises distributed analysis of particulate activity in such a process.

BACKGROUND OF THE DISCLOSURE

There are numerous industrial processes which take in raw or first intermediate materials at one end, perform some kind of operation on the material (for example mixing, treating with heat or pressure or chemically altering the material) to produce a second intermediate or end material or product.

Examples of such processes are:
Processing of foodstuffs, including beverages;
Processing of water (for human consumption, as a raw material for liquid products, industrial process water, cleaning water, waste water and other uses);
Processing of household and industrial chemicals;
Processing of petrochemical products;
Processing of cosmetic products;
Processing of pharmaceutical products;
Processing of oil and gas-related products;
Processing of paints and coatings;
Processing of pulp and paper related products; and
Processing of powder slurries (such as calcium carbonate or titanium dioxide slurries and other powders).

At least an embodiment of the present disclosure is particularly well suited to the processing of liquid materials, and in particular paints, but may be used for any of the processes above.

In the technical field of paint processing, several raw materials are provided at a first end of the process. These include fillers, dispersants, pigments, latex, and acrylic, which must be mixed and treated in several stages before an end product is produced, which is placed in tins to be shipped to customers. During this process, the various materials (in liquid form) are passed through long sections of pipework, and in and out of tanks. In any given process there may be several kilometres of pipework between the introduction of the raw materials and the final paint product.

It is highly undesirable for microbial activity to take place within the process. Production of paint with a high microbial load is unacceptable, and can cause significant problems for the end user (such as an unpleasant odour).

Therefore it is important to check the microbial load in the paint produced by this process on a regular basis.

Until recently, it has been possible to treat the liquid in the process with high amounts of biocide. This effectively kills any microbes which may have an adverse effect on the product. That said, it is generally undesirable to use a high quantity of biocide. Further, recent legislation (in the form of the EU Biocide Regulation) has placed significant limits on the types and amounts of biocide that can be used. Similar regulations exist in the United States of America and most other important economic centres.

Currently, detection of microbial activity is assessed by taking a sample of paint at the end of the process. The sample is sent to a lab to be analysed. Information concerning the microbial load may be delivered some days or weeks later. Detection of an excess of microbial activity would result in the plant being shut down and cleaned, and the affected paint recalled form the market and disposed of. Evidently the reduction in the use of biocides increases the risk that a sample is contaminated.

Systems such as the applicant's CFII (CellFacts II) device help to increase the speed at which microbial activity can be detected and corrective action initiated before microbial levels can reach critical levels. The CFII device is a combined impedance and fluorescence particle detection system. The liquid to be analysed is diluted, exposed to a suitable fluorescent dye and passed through an orifice. Changes in impedance are measured to detect particle size, and a laser is used to excite the dye and determine particle fluorescence. In this way, the size and type of particles can be detected, which information can be used to estimate microbial activity. The cycle takes less than three minutes. Such a system is discussed in GB2380792 which is incorporated by reference herein where permitted.

Although the CFII system has radically improved analysis times (a matter of minutes rather than days), it is only used in a "batch" context. In other words, the system is used to analyse the end-product, and determine if microbial load is unacceptable. If it is, then the batch needs to be either treated or disposed of, and the system cleaned.

What is required is a method and system which overcomes, or at least mitigates, the above problems.

BRIEF DESCRIPTION OF THE EXEMPLARY EMBODIMENTS

An exemplary embodiment of an apparatus for the detection of microbiological activity in an industrial process may include a plurality of satellite units, a processing unit, and a main analysis unit. Each satellite unit may be configured to sample a liquid from the industrial process at a plurality of respective locations, periodically analyse a sample, carry out an impedance analysis to count and measure the size of particles passing through an orifice, and generate sample results data corresponding to the number and size of particles in each sample. The processing unit may be configured to compare the sample results data to a predetermined criterion and to generate an alert signal if the particle data is outside of the predetermined criterion. The main analysis unit may be configured to carry out a combined impedance and electromagnetic emission analysis of a sample of liquid from the industrial process following generation of the alert signal.

An exemplary embodiment of a method of monitoring microbiological activity in an industrial process may include providing a plurality of satellite units and a main analysis unit. The plurality of satellite units may be provided at a plurality of respective locations. Each satellite unit may be configured to carry out an impedance analysis to count and measure the size of particles passing through an orifice. The main analysis unit may be configured to carry out a combined impedance and electromagnetic emission analysis.

The method may further include using the satellite units to periodically sample a liquid from the industrial process, generating sample results data corresponding to the number and size of particles in each sample, and comparing the sample results data to a predetermined criterion. The method may further include, in response to the sample results data being outside the predetermined criterion or establishing a trend approaching the predetermined criterion, using the main analysis unit to analyse a sample of liquid from the industrial process to determine the biological activity in the sample.

An exemplary embodiment of an apparatus for regular sampling of a liquid in an industrial process may include a fluid take-off connectable to a liquid conduit, a metering assembly configured to meter a predetermined amount of liquid from the fluid-take-off, a dilution assembly configured to dilute at least part of the predetermined amount of liquid to form an analysis sample, an analysis unit configured to pass the analysis sample through an orifice and to undertake impedance-based particle analysis on the sample to thereby determine the number and size of particles within the analysis sample, and a memory configured to store sample results relating to the number and size of particles within the analysis sample.

BRIEF DESCRIPTION OF THE FIGURES

A more particular description will be rendered by reference to exemplary embodiments that are illustrated in the accompanying figures. Understanding that these drawings depict exemplary embodiments and do not limit the scope of this disclosure, the exemplary embodiments will be described and explained with additional specificity and detail through the use of the accompanying drawings in which.

Various features, aspects, and advantages of the exemplary embodiments will become more apparent from the following detailed description, along with the accompanying drawings in which like numerals represent like components throughout the figures and detailed description. The various described features are not necessarily drawn to scale in the drawings but are drawn to emphasize specific features relevant to some exemplary embodiments.

The headings used herein are for organizational purposes only and are not meant to limit the scope of the disclosure or the claims. To facilitate understanding, reference numerals have been used, where possible, to designate like elements common to the figures.

DETAILED DESCRIPTION

Reference will now be made in detail to various exemplary embodiments. Each example is provided by way of explanation and is not meant as a limitation and does not constitute a definition of all possible embodiments.

Figure 1:
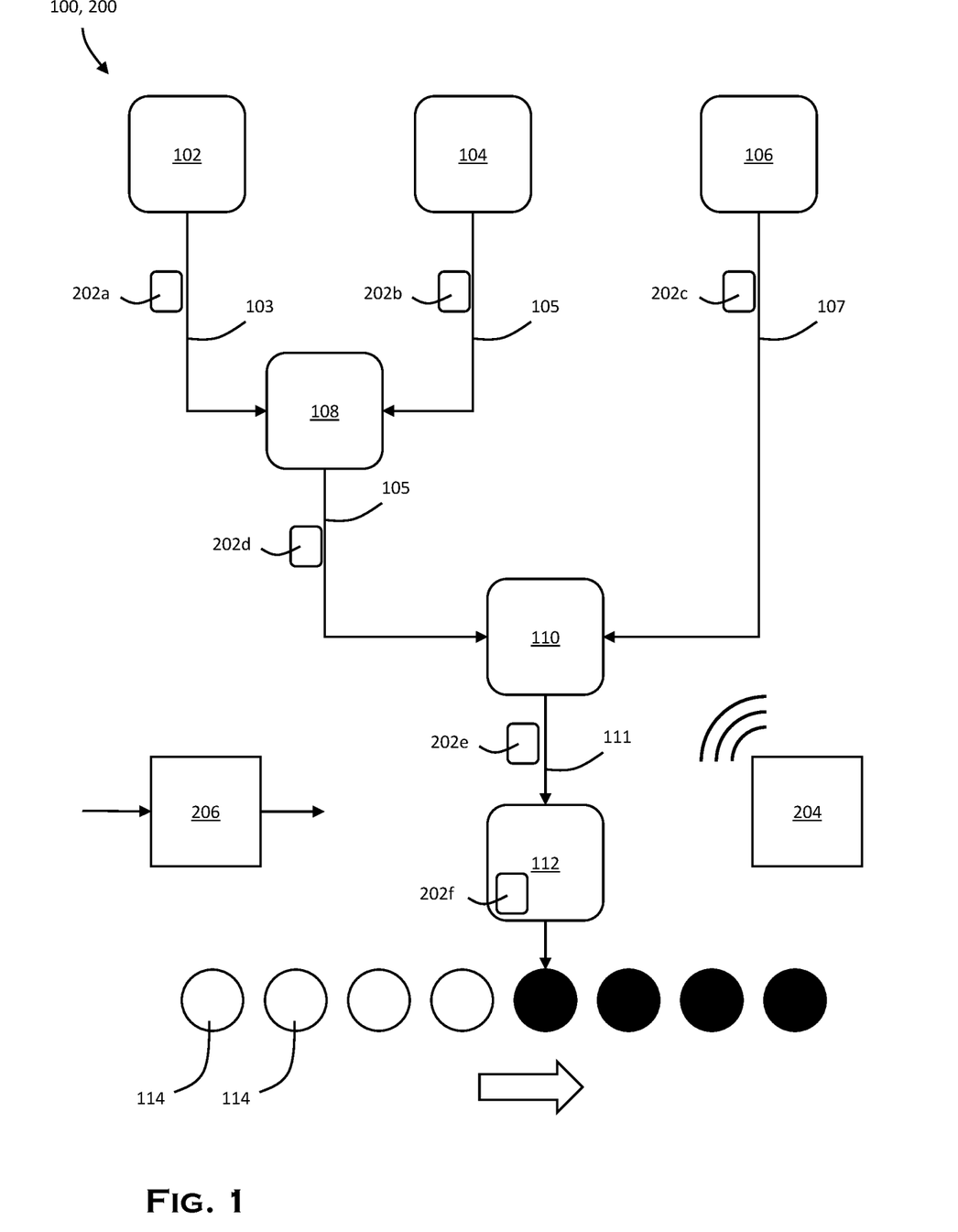
FIG. 1 is a schematic view of a first apparatus according to an exemplary embodiment employed in an industrial process.

Referring to FIG. 1, a schematic and simplified plan view of a paint processing production line 100 is shown. The line 100 comprises three storage tanks 102, 104, 106 each containing a different raw material. Each tank has a respective outflow channel in the form of storage tank outflow pipes 103, 105, 107. The pipes 103, 105 connect the storage tanks 102, 104 to a first mixing tank 108 which mixes the raw materials from the storage tanks 102, 104. The first mixing tank has an outflow channel in the form of a first mixing tank outflow pipe 109.

The first mixing tank outflow pipe 109 flows into a second mixing tank 110. The third storage tank outflow pipe 107 also flows into the second mixing tank 110, where the materials are mixed. The second mixing tank 110 has a second mixing tank outflow pipe 111 which flows into a final storage tank 112.

The final storage tank 112 is configured to sequentially fill a plurality of individual containers in the form of paint pots 114 which are sealed and shipped to the customer.

Each of the above components is typically constructed from steel, specifically a stainless steel.

Apparatus

An apparatus according to an exemplary embodiment is distributed throughout the line 100 in FIG. 1, and is generally referred to as apparatus 200. The apparatus 200 comprises:

A plurality of satellite units 202a, 202b, 202c, 202d, 202e, 202f;

A controller 204; and,

An analysis unit 206.

Each of the above components will be described in detail. Satellite Units 202a, 202b etc.

Figure 2:
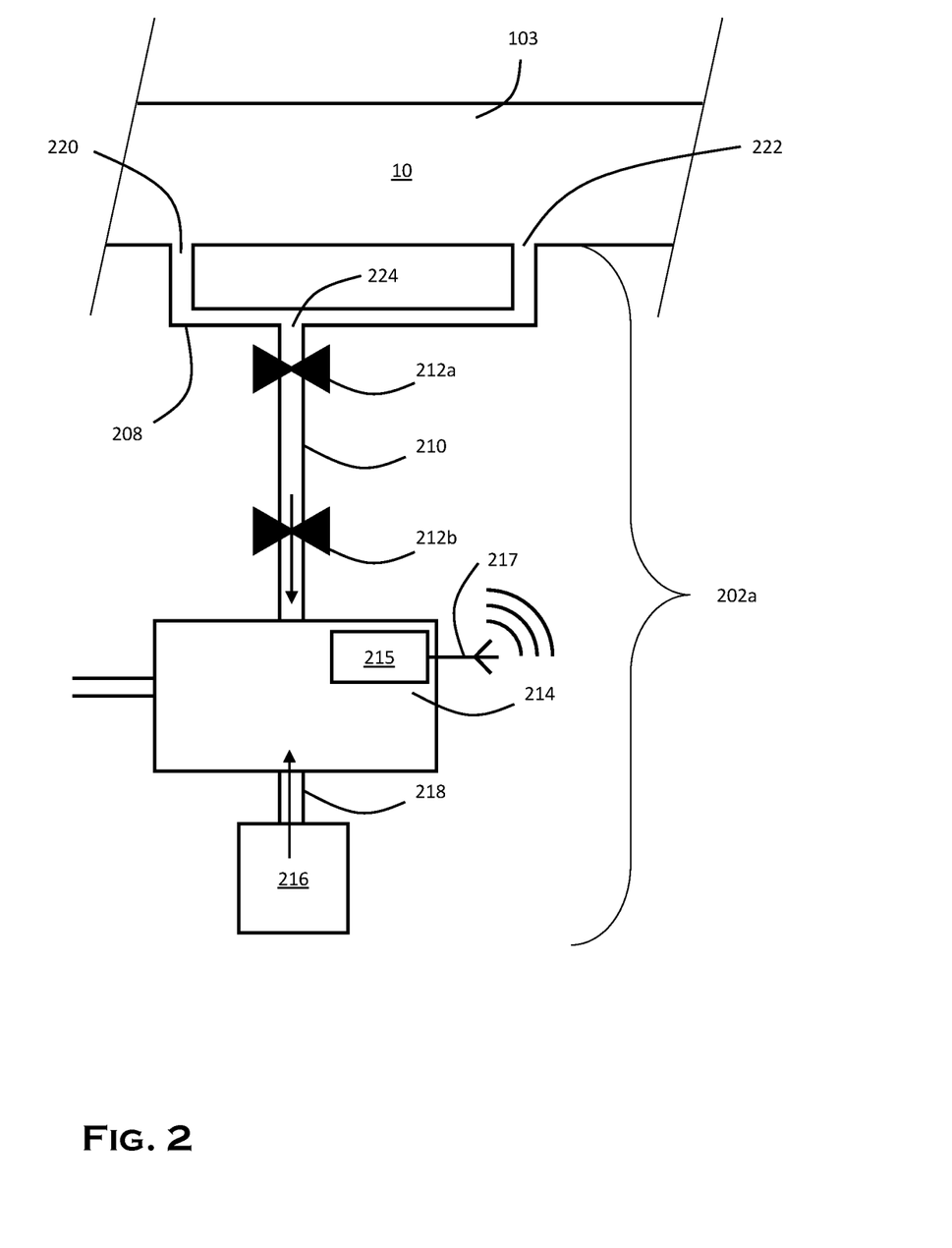
FIG. 2 is a view of a subassembly of the apparatus of FIG. 1.

Referring to FIG. 2, a satellite unit 202a is shown in more detail. The satellite units are very similar, and as such only the unit 202a is shown.

The unit 202a comprises a flow loop 208, a sample flow channel 210, valves 212a, 212b, satellite analyser 214 and dilutant tank 216 having dilutant flow channel 218.

The flow loop 208 comprises an entry point 220 and exit point 222 both in fluid communication with the storage tank outflow pipe 103. The pipe 103 contains a fluid 10 under pressure. Because the exit point 222 is downstream of the entry point, a flow is established in the flow loop 208.

The sample flow channel 210 has an entry opening 224 in fluid communication with the flow loop 208, and flows into the satellite analyser 214. The valves 212a, 212b can be selectively opened and closed (by a controller of the satellite analyser) to feed a discrete sample of liquid to the analyser 214 of known volume (in this example 1 ml).

The satellite analyser 214 comprises several controlled valve-controlled flow channels and is configured to meter dilutant from the tank 216 via the channel 218 to dilute the sample to e.g. 20 ml in volume. A small amount of diluted sample (approximately 100 µl) is then passed through an orifice to both count and size the particles therein using impedance analysis. The satellite analyser comprises a controller 215 having a processor, memory and communication means in the form of an antenna 217 which is configured to communicate with the system controller 204.

Impendence analysis has been used in the art, and for example is explained in the applicant's prior application EP0844475 (incorporated by reference herein where permitted). In summary, the orifice has a pair of electrodes disposed on opposite sides thereof. The analyser comprises circuitry capable of measuring a signal representative of the impedance variation between the electrodes. The diluent (typically an electrolyte) has a known impendence across the orifice. As particles pass through the orifice, the impendence will increase and then decrease. Each "peak" represents a particle, and the height of the peak and/or area under the peak is representative of particle size. Because the orifice is very small (in the order of 30 μm), only one particle can pass through at any given time.

The satellite controller 215 stores results data for each sample, and is configured to communicate the assay results data (representative of the size and number of particles passing through the orifice) to the system controller 204 via the antenna 217.

Once the sample has been analysed, the system is flushed, and a further sample is taken. The satellite units sample at a frequency of 20 minutes.

It is important to note that the satellite analysers 214 only use impedance measurement, and do not (in this embodiment) comprise means for measuring fluorescence. They are therefore simple and inexpensive.

Controller 204

The controller 204 comprises a processor, memory and display unit. In this embodiment, it is a PC. As discussed above, each satellite analyser is in communication with the controller 204. This may be via a wired connected, or wireless such as Wi-Fi, Bluetooth® or similar technology. Results data from the sample impendence assay are communicated to the controller 204 which carries out analysis of the data.

Analysis Unit 206

The analysis unit 206 combines both impedance analysis with fluorescence analysis. The analysis unit 206 is similar to the applicant's CFII device discussed above, and as well as impedance measurement undertakes fluorescence analysis using a laser. This can determine whether fluctuations in particle size and number are a symptom of a chemical process or a biological process.

Method of Operation

Once the production line 100 is started, material flows from the raw material storage tanks 102, 104, 106 through the system to the final storage tank 112. Each satellite unit 202a etc. samples the material flowing through each pipe at regular (20 minute in this embodiment) intervals. Each satellite unit 202a etc. communicates assay results data for each sample to the controller 204.

The controller 204 contains baseline data representative of an acceptable number and size distribution of particles for each satellite unit. An example baseline for satellite unit 202a is shown as curve B in an S-N graph 300 in FIG. 3. The X-axis represents the size of the particles (S) and the Y-axis the number (N) of particles of that size. The baseline data may be obtained by calibration- i.e. by analysing a sample with a known/acceptable level of microbial activity, or from stored data. It will be noted that a certain number and size distribution of particles is expected-notwithstanding the presence of microbes, any given sample will contain chemical (non-biological) particles which are not of concern.

Figure 3:
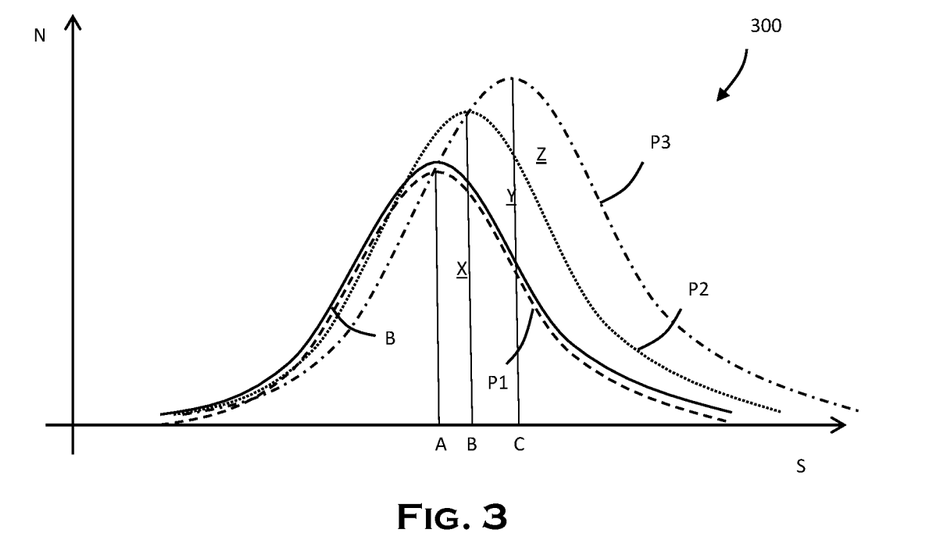
FIG. 3 is a graph of analysis results from the subassembly of FIG. 2.

A first result from satellite unit 202a is shown as profile P1 in FIG. 3, which is within a predetermined, acceptable range of the baseline B. The manner in which an acceptable deviation from B is determined may be selected by the skilled addressee without undue burden, and based on known statistical methods. In this example, for ease of understanding, two parameters will be used- the X axis coordinate of the curve peak (the size of the particles highest in number, or the mode average, of the sample), and the area under the curve (representative of the total number of particles in the sample). If microbiological activity increases, it will be expected that both will increase in subsequent samples.

The peak of P1 (A) is shown as well as the area (X). This data is represented in the first row of a results table 302 of FIG. 4, stored by the controller 204 for each satellite unit. Referring to FIG. 5, a visual display graphic 304 provided by the controller 204 for satellite unit 202a is shown. The graphic 304 has a time axis (x-axis) and a particle count axis (y axis). Three bands of particle count are provided, coloured green (low count), yellow (medium count) and red (high count). Sample data points are plotted and the operator can easily identify a trend towards an unacceptable particle count (red) and take remedial action (as will be discussed below). In reality, multiple curves (one per satellite unit) may be shown on the graphic 304. Further graphics with different parameters may also be shown on the controller display.

Figure 4:
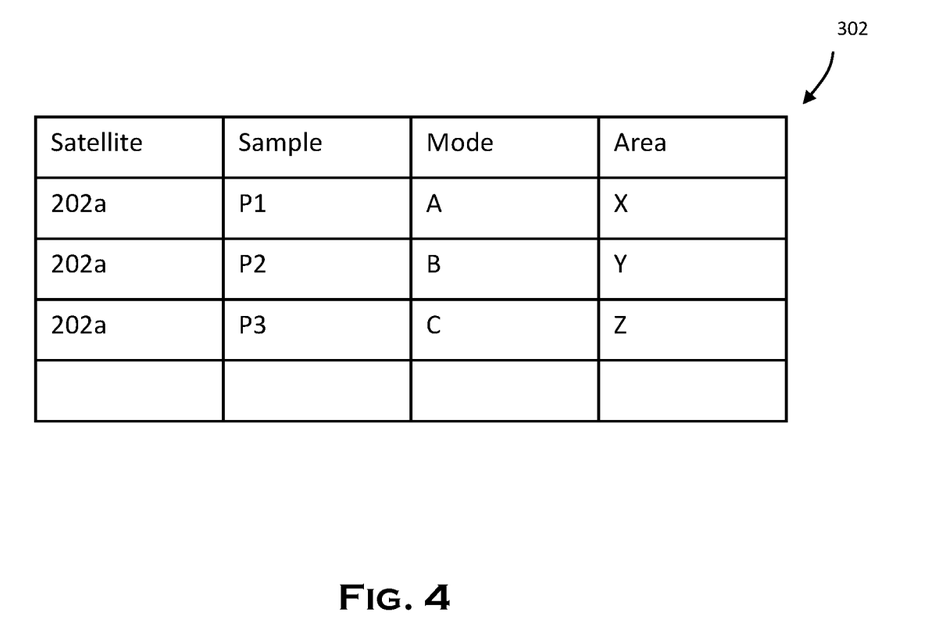
FIG. 4 is a table of summary results from the subassembly of FIG. 2.
Figure 5:
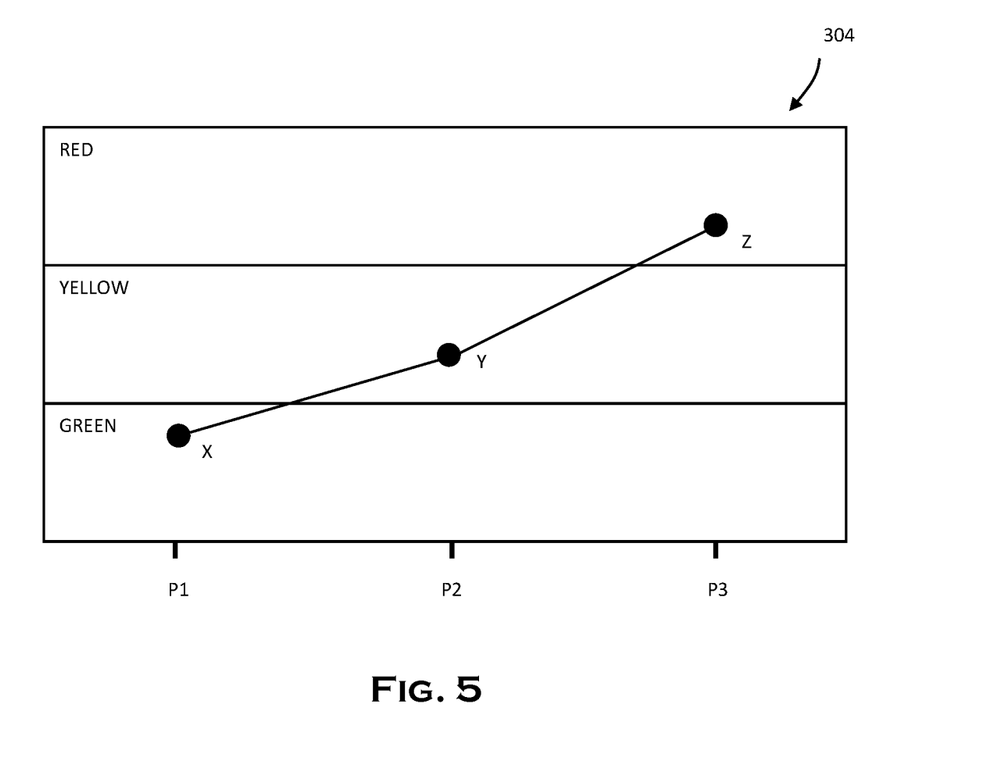
FIG. 5 is a display from the controller of the apparatus of FIG. 1.

A further profile P2 is shown in FIGS. 3 to 5 in which the particles have grown in both size and number (the peak has increased from A to B, and the number from X to Y). Moving on to P3, size and number have increased again (from B to C, and Y to Z).

The operator can clearly see from the display 304 that the trend at satellite unit 202a indicates an increase in particle size and count. This may be indicative of microbial activity, or a symptom of a chemical process taking place which is out of the ordinary. As soon as the monitored parameter or parameters enter the red zone, an alert is produced.

At this point, the operator takes a sample from the location of the satellite unit 202a and takes it to the analysis unit 206 for combined impedance/fluorescence analysis. This combined analysis determines conclusively whether the increased size and number of particles is a result of increased microbiological activity. If it is, the operator adds a biocide upstream of the satellite unit in question.

For example, if the satellite unit 202a detects high microbial activity, the problem likely lies with the raw material in the tank 102. Either the material can be replaced (following cleaning), switched to a different tank or a biocide can be added.

In the event that e.g. biocide is added to the tank 102, the satellite unit is used to verify its effectiveness. The trend in increase in size and number of particles will reverse (i.e. move back into the "yellow" and "green" zones). This occurs as the biocide lyses the microbial cells.

If it does not, the satellite unit will communicate this to the controller. At this point, the operator can attempt to increase the dose, or change the type of biocide used. Alternatively, he or she can carry out a more detailed biocide effectiveness test series as will be discussed below.

It will be noted that the system described herein can pinpoint the source of microbial contamination which means that targeted remedial action can be taken. This represents a significant increase in efficiency.

Detailed Biocide Effectiveness Test Series

According to an exemplary embodiment, the combined impendence/fluorescence analyser can be used to study the efficacy of various biocides until an appropriate solution is found.

Figure 6:
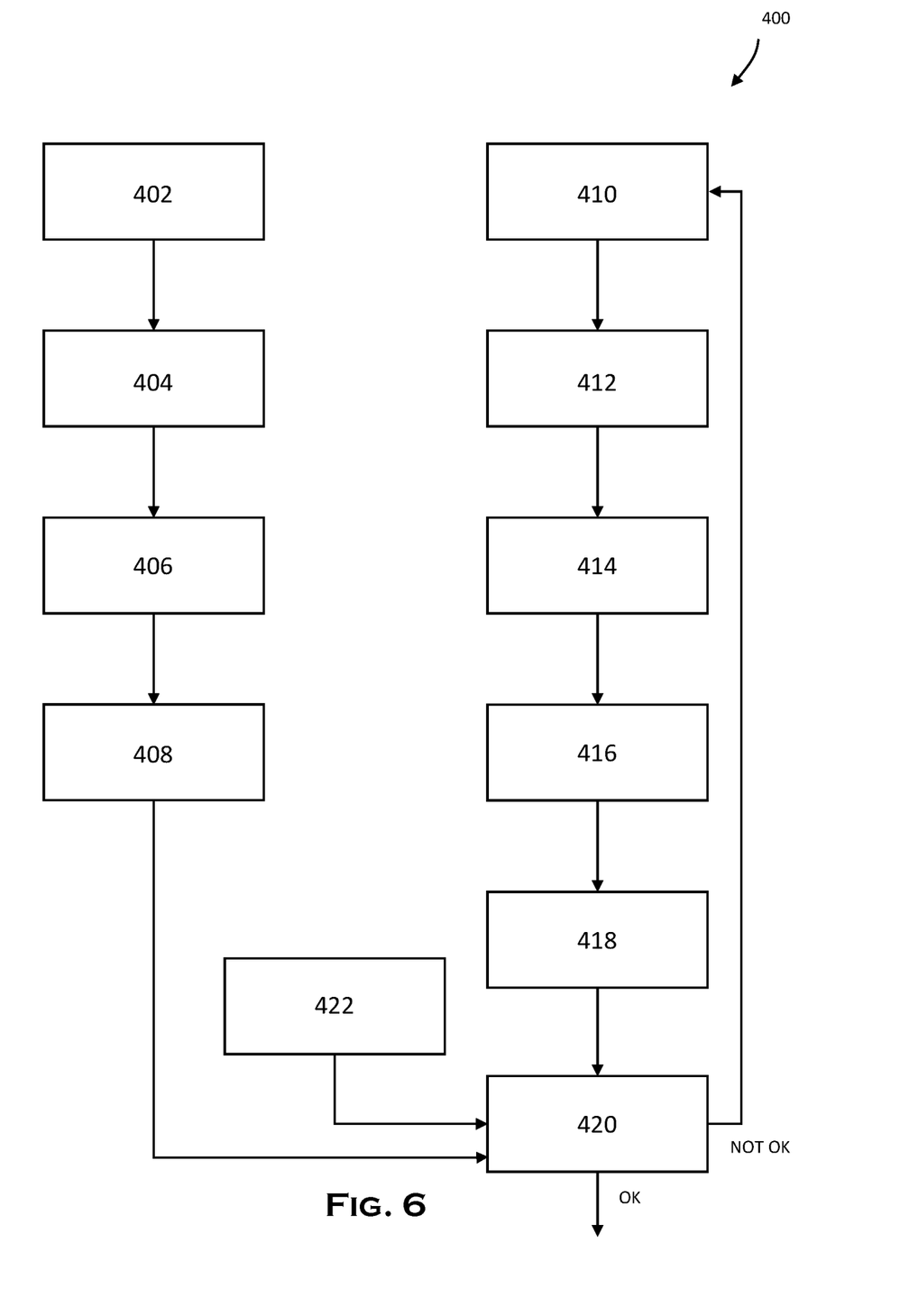
FIG. 6 is a flow chart of a method according to an exemplary embodiment.

Referring to FIG. 6, such a process 400 is shown. At step 402, a sample is taken from a batch of material having high/unacceptable microbial activity. At step 404 it is introduced into the combined impedance/fluorescence analyser (such as a CFII). At step 406, the sample is analysed and at step 408 the biological activity assessed based on the result.

At step 410, a further sample is taken from the batch. At step 412 a biocide is added. At step 414 it is introduced into the combined impedance/fluorescence analyser (such as a CFII). At step 413, the sample is analysed and at step 418 the biological activity assessed based on the result.

The results from the biocide assay are then compared both to the original sample (without biocide) from step 408, and to a baseline set of results 422. If the biocide has reduced the microbial activity from the original sample 408, and is within a predetermined tolerance of the baseline data 422 the biocide dosage regime is deemed "OK" and the same concentration and type can be used to treat the entire batch.

If the microbial activity has not decreased, or decreased to a level which remains unacceptable compared to the baseline, the method returns to step 410 to try a different biocide and/or higher concentration.

As such, the analyser can be used iteratively to determine the most effective biocide regime for the batch.

As such the analyser can also be used to support and accelerate the experiments required by standardised challenge tests.

Variations

Variations fall within the scope of the present disclosure.

The system 200 may be configured as a fully automated closed-loop system. An automatic biocide dispenser may be provided upstream of at least one satellite unit and automatically activated as the controller 204 detects a particle parameter moving out of the predetermined range.

The satellite units do not need to connect to a central controller, but may instead produce a local alert signal (such as a visual or audible alert). This may then prompt the operator to conduct a full impendence/fluorescence test. The system is capable of generating results data on individual measurements to establish whether or not predetermined criteria, such as critical levels of microbial load and activity are breached.

The system is also capable of establishing whether or not a series of successive results data is forming a trend, indicating that predetermined criteria may be reached soon. As such the system is capable of anticipating or predicting a microbial contamination at an early stage and to initiate measured corrective action.

Advantageously, utilising a combination of satellite units distributed throughout the process line which perform impendence-based analysis may yield several beneficial results. For example:

System cost is kept under control. At least an embodiment of the present disclosure can be performed with impendence-only satellite units as early warning sensors, which are less expensive than combined impedance/fluorescence units, which are only needed for in-depth analysis if the microbial load in the product reaches critical threshold levels;

System responsiveness is increased. The satellite units can sample on a very regular basis (say, every 20 minutes) which reduces the time to detection of a problem; and, System intelligence is increased. Use of distributed satellite units means that the location of a problem can be determined, and targeted action can be taken.

The combination of a number of satellite units with a main analysis unit (with combined impedance and fluorescence) yields a much higher-performing system than the prior art approach.

This disclosure, in various embodiments, configurations and aspects, includes components, methods, processes, systems, and/or apparatuses as depicted and described herein, including various embodiments, sub-combinations, and subsets thereof. This disclosure contemplates, in various embodiments, configurations and aspects, the actual or optional use or inclusion of, e.g., components or processes as may be well-known or understood in the art and consistent with this disclosure though not depicted and/or described herein.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

In this specification and the claims that follow, reference will be made to a number of terms that have the following meanings. The terms "a" (or "an") and "the" refer to one or more of that entity, thereby including plural referents unless the context clearly dictates otherwise. As such, the terms "a" (or "an"), "one or more" and "at least one" can be used interchangeably herein. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower" etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while considering that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that the appended claims should cover variations in the ranges except where this disclosure makes clear the use of a particular range in certain embodiments.

The terms "determine", "calculate" and "compute," and variations thereof, as used herein, are used interchangeably and include any type of methodology, process, mathematical operation or technique.

This disclosure is presented for purposes of illustration and description. This disclosure is not limited to the form or forms disclosed herein. In the Detailed Description of this disclosure, for example, various features of some exemplary embodiments are grouped together to representatively describe those and other contemplated embodiments, configurations, and aspects, to the extent that including in this disclosure a description of every potential embodiment, variant, and combination of features is not feasible. Thus, the features of the disclosed embodiments, configurations, and aspects may be combined in alternate embodiments, configurations, and aspects not expressly discussed above. For example, the features recited in the following claims lie in less than all features of a single disclosed embodiment, configuration, or aspect. Thus, the following claims are hereby incorporated into this Detailed Description, with each claim standing on its own as a separate embodiment of this disclosure.

Advances in science and technology may provide variations that are not necessarily express in the terminology of this disclosure although the claims would not necessarily exclude these variations.

The invention claimed is:

1. An apparatus for the detection of microbiological activity in an industrial process, the system comprising:
 a plurality of satellite units configured to:
  sample a liquid from the industrial process at a plurality of respective locations,
  periodically analyse a sample,
  carry out an impedance analysis to count and measure the size of particles passing through an orifice, and
  generate sample results data corresponding to the number and size of particles in each sample;
 a processing unit configured to compare the sample results data to a predetermined criterion and to generate an alert signal in response to the particle data being outside of the predetermined criterion; and,
 a main analysis unit configured to carry out a combined impedance and electromagnetic emission analysis of a sample of liquid from the industrial process following generation of the alert signal.

2. The apparatus according to claim 1, wherein the processing unit is a system controller configured to receive results data from each of the plurality of satellite units.

3. The apparatus according to claim 2, wherein the system controller is configured to:
 process the results data to obtain at least one results parameter, and
 generate the alert signal in response to the results parameter being outside the predetermined criterion.

4. The apparatus according to claim 3, wherein the at least one results parameter is indicative of the number of particles in the respective sample.

5. The apparatus according to claim 3, wherein the at least one results parameter is indicative of the average size of particles in the respective sample.

6. The apparatus according to claim 1, wherein each satellite unit is configured to analyse a sample every N minutes, where N<60.

7. The apparatus according to claim 1, wherein each satellite unit comprises an automatic sample take-off assembly configured to periodically extract a sample from the industrial process.

8. The apparatus according to claim 1, wherein the main analysis unit is configured to carry out a combined impedance and fluorescence analysis.

9. A method of monitoring microbiological activity in an industrial process, comprising:
 providing:
  a plurality of satellite units at a plurality of respective locations, each satellite unit being configured to carry out an impedance analysis to count and measure the size of particles passing through an orifice;
  a main analysis unit configured to carry out a combined impedance and electromagnetic emission analysis;
 using the satellite units to periodically sample a liquid from the industrial process;
 generating sample results data corresponding to the number and size of particles in each sample;
 comparing the sample results data to a predetermined criterion, and, in response to the sample results data being outside the predetermined criterion or establishing a trend approaching the predetermined criterion, using the main analysis unit to analyse a sample of liquid from the industrial process to determine the biological activity in the sample.

10. The method according to claim 9, wherein the electromagnetic emission analysis is fluorescence analysis.

11. The method according to claim 9, further comprising:
 generating an alert signal in response to the sample results data being outside the predetermined criterion or establishing a trend approaching the predetermined criterion.

12. The method according to claim 9, wherein the processing unit is a system controller, and further comprising:
 transmitting sample results data from the plurality of satellite units to the system controller.

13. The method according to claim 9, further comprising:
 using the system controller to process the results data to obtain at least one results parameter.

14. The method according to claim 13, wherein the at least one results parameter is indicative of the number of particles in the respective sample.

15. The method according to claim 14, wherein the at least one results parameter is indicative of the average size of particles in the respective sample.

16. The method according to claim 9, wherein each satellite unit is configured to analyse a sample every N minutes, where N<60.

17. The method according to claim 9, wherein each satellite unit comprises an automatic sample take-off assembly, configured to periodically extract a sample from the industrial process.

18. The method according to claim 9, further comprising, in response to the using the main analysis unit indicating unacceptable biological activity, introducing a biocide to the industrial process.

19. The method according to claim 18, further comprising:
 using at least one satellite unit to monitor the effectiveness of the biocide.

20. An apparatus for regular sampling of a liquid in an industrial process, the apparatus comprising:
 a fluid take-off connectable to a liquid conduit;
 a metering assembly configured to meter a predetermined amount of liquid from the fluid-take-off;

a dilution assembly configured to dilute at least part of the predetermined amount of liquid to form an analysis sample;

an analysis unit configured to pass the analysis sample through an orifice and to undertake impedance-based particle analysis on the sample to thereby determine the number and size of particles within the analysis sample; and a memory configured to store sample results relating to the number and size of particles within the analysis sample.

\* \* \* \* \*